United States Patent [19]

Rosati et al.

[11] Patent Number: 4,681,108
[45] Date of Patent: Jul. 21, 1987

[54] CIRCULAR MECHANICAL ANASTOMOTIC GUN

[76] Inventors: Riccardo Rosati, Via Livorno, 4, Milano; Carlo Rebuffat, Via Galilei, 17, Trento, both of Italy

[21] Appl. No.: 701,150
[22] Filed: Feb. 13, 1985
[30] Foreign Application Priority Data
Feb. 16, 1984 [IT] Italy .............................. 19653 A/84
[51] Int. Cl.$^4$ ............................................. A61B 17/04
[52] U.S. Cl. ................................................ 128/334 R
[58] Field of Search ...................... 128/305, 334, 335; 227/DIG. 1

[56] References Cited
U.S. PATENT DOCUMENTS 4,207,898  6/1980  Becht .............................. 128/334 R
4,304,236 12/1981  Conta et al. ......................... 128/305
4,351,466  9/1982  Noiles ............................. 128/334 R
4,476,863 10/1984  Kanshin et al. .................. 128/334 R
4,505,272  3/1985  Utyamyshev et al. ......... 128/334 R Primary Examiner—Richard C. Pinkham
Assistant Examiner—Gary Jackson

[57] ABSTRACT

A mechanical gun for circular anastomosis of hollow organs by which the elements of a particular suturing device are engaged one into the other compressing between their walls the tissue edges of two resected hollow organs. The gun also comprises a circular cutting member which trim outside the compression area inside the device the edges of the compressed tissues, and then releases the circular mechanical gun from the suturing device which will be maintained until a natural suture forms between the connected hollow organs.

4 Claims, 3 Drawing Figures

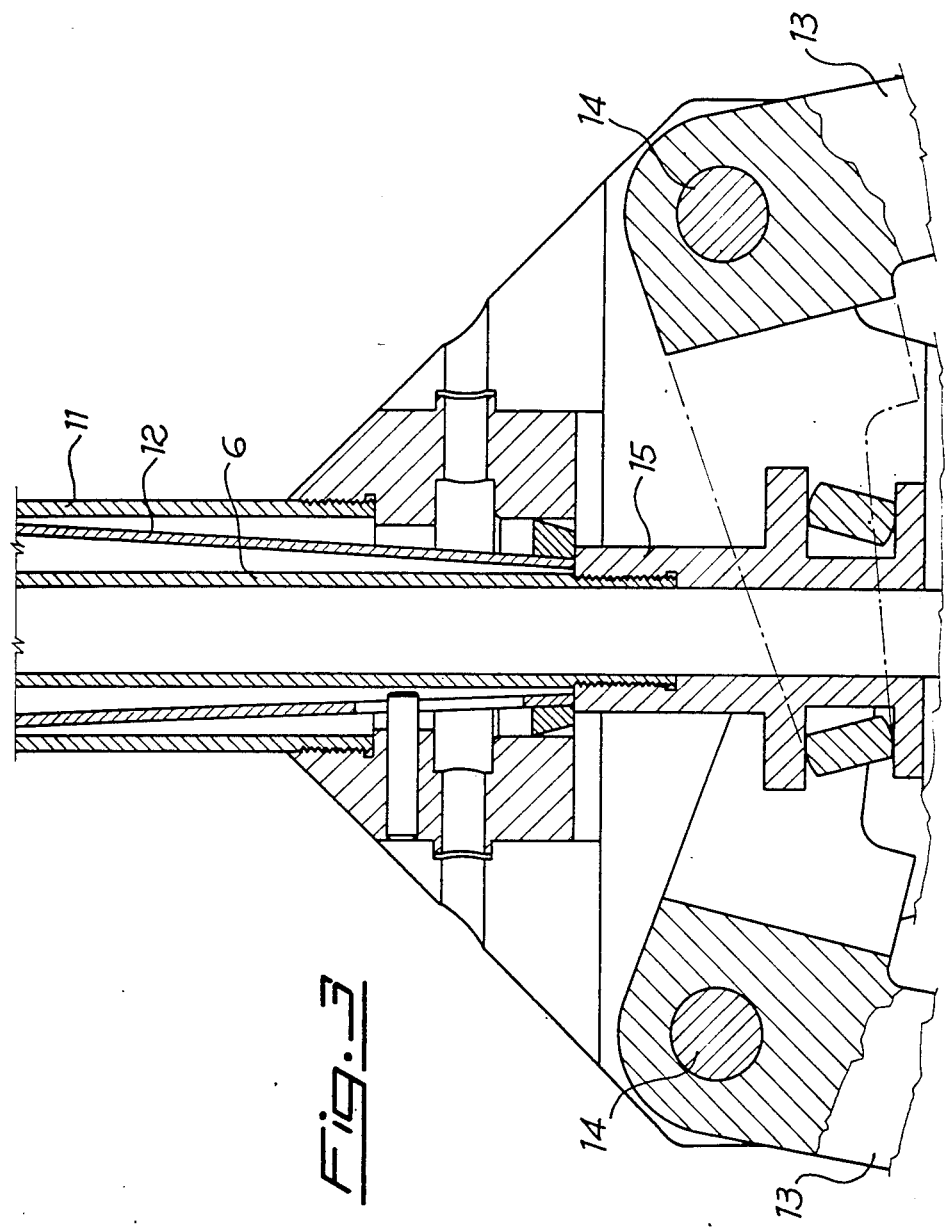

CIRCULAR MECHANICAL ANASTOMOTIC GUN

BACKGROUND OF THE INVENTION

The present invention is directed to a new mechanical gun suitable to perform circular anastomosis in hollow organs.

Circular mechanical guns are known in the art, and such guns utilize for joining the tissue edges of the resected hollow organs a system of metallic staples which are inserted from inside the hollow organ, into the overlapped tissues of the two hollow organ edges and are rivetted inwards to achieve the anastomosis.

Another known circular mechanical anastomotic gun includes a particular system consisting of partially metallic and partially plastic flat rings kept together by a system of connecting nails with coaxial springs to achieve the anastomosis by compression applied to the tissue edges of the specific dissected hollow organs.

SUMMARY OF THE INVENTION

The circular mechanical anastomotic gun of the present invention achieves the anastomosis in the digestive system using a compression device which is the subject of patent application Ser. No. 701,207 filed by Applicants at even date with the present application, now U.S. Pat. No. 4,598,712.

This anastomosis device comprises three coaxial elements of a particular shape which realize the compression of the hollow organ dissected tissues between the walls of two of such elements, said compression being applied suitably by inserting the third element into the second one.

After a certain period of time has elapsed, the compressed tissues necrotize and fall inside the hollow organ thereby disconnecting the device causing the compression from the organ. Both are naturally eliminated whilst in that interval of time the anastomosis of the faced tissues immediately outside the area where the pressure is applied, occurs.

BRIEF DESCRIPTION OF THE DRAWINGS

FIG. 3 is an enlarged side view of the central portion of FIG. 1.

DETAILED DESCRIPTION OF THE INVENTION

The mechanical gun for circular anastomosis, forming the object of the present invention is essentially formed by three parts:

(1) A head portion consisting of two parts: the first one, at one end, having a broad size, the second one having a cylindrical shape.

The broad part carries a device able to perform the anastomosis by compression, and a cutting member which allows the mechanical gun to disengage from the organs when the suturing is completed for allowing the withdrawal of the same from inside the hollow organ. The cylindrical part is formed by a central pivot which is the axis of the whole circular mechanical anastomotic gun and makes it possible to introduce the gun end portion into the dissected hollow member.

The central pivot is surrounded by a system of concentric tubular elements which support the outer and the intermediate element of the compression device; the median, the element of the compression device which if inserted into the intermediate element and lastly the inner one which supports the cutting member. The last two tubular elements, i.e. the inner and the median ones, are operated by a differentiated motion allowing the cutting member to continue its stroke even when the median cylindrical element carrying the compression device stops.

(2) A median portion crossed by the central pivot, provided with mechanical means capable of imparting a slipping movement between the end portion and the central pivot during an anastomosis.

(3) A end portion crossed by the central pivot, formed by a cylindrical terminal part carrying a knob able to realize, by its rotation, the slipping of the central pivot as to the whole machine. Said portion is provided with an outer scaled groove to indicate such slipping.

Figure 1:
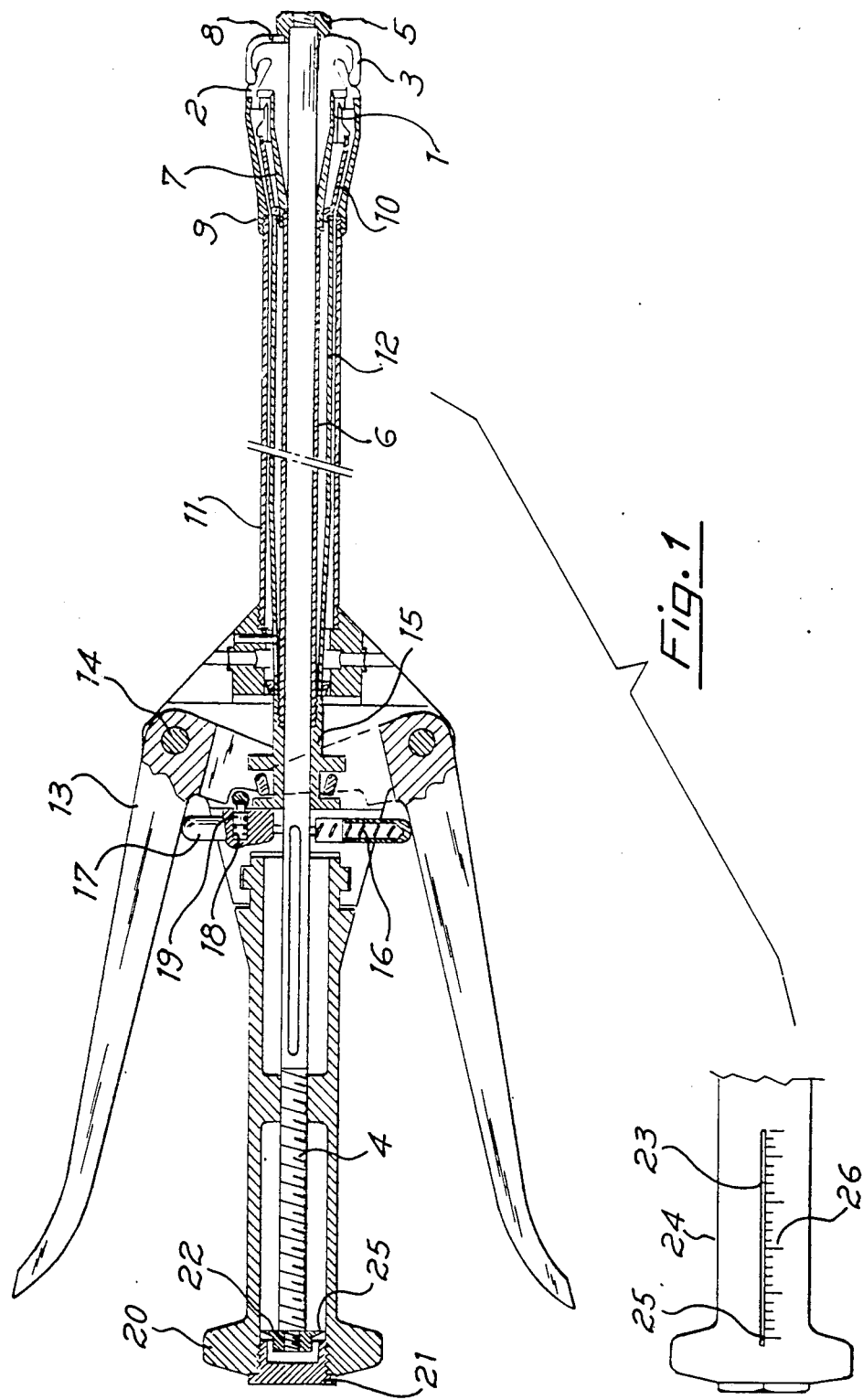
FIG. 1 is a side view of a preferred embodiment of the invention of a circular mechanical anastomotic gun.

FIG. 1 represents a section view of the anastomotic gun in a rest position having inserted the compression suturing device formed by the elements 1, 2 and 3, the last two being already connected. There is shown: in the head portion, the central pivot 4 carrying the device 5 capable of stopping the element 3. The coaxial cylinder 6, inside of which the central pivot 4 extends. A thread connects the pivot 4 to the circular blade 7 which, when moved by operation of the median portion device contacts the element 3 and cuts it along the groove 8 therein prearranged to facilitate the cut. In this way, a port having a diameter bigger than that of the stop element 5 is defined so that the element 3 can slip through said port allowing the circular mechanical anastomotic gun to be disengaged. The elements 9 and 10 are connected by a threaded connection respectively to the tubular bodies 11 and 12, which are coaxial to the central pivot 4, and carry the elements 2 and 1 respectively.

In the median portion the lever arms 13 pivoted on the pivot 14, allow operation of the body 15, whcih is coaxial with the central pivot by transmitting movement to the circular blade 7 and to the element 1. The springs 16, when compressed inside the cylindrical holders 17, maintain the lever arms 13 in an open position whilst the spring 18 by means of the prong 19 operates the device safety gear.

In the end portion the central pivot 4 is partially threaded so that rotation of the knob 20 causes the locking nut 21 to slip against corresponding device parts.

A cap nut 22 is threadably attached to the very end of the central pivot 4 threaded part, and the cap nut 22 is shaped so that it can be viewed through the longitudinal slit 23, (detail in FIG. 1) on the circular member 24 an index 25 is located on the device for the amount of central pivot 4 slip with respect to all the other parts of the mechanical anastomotic gun.

Figure 2:
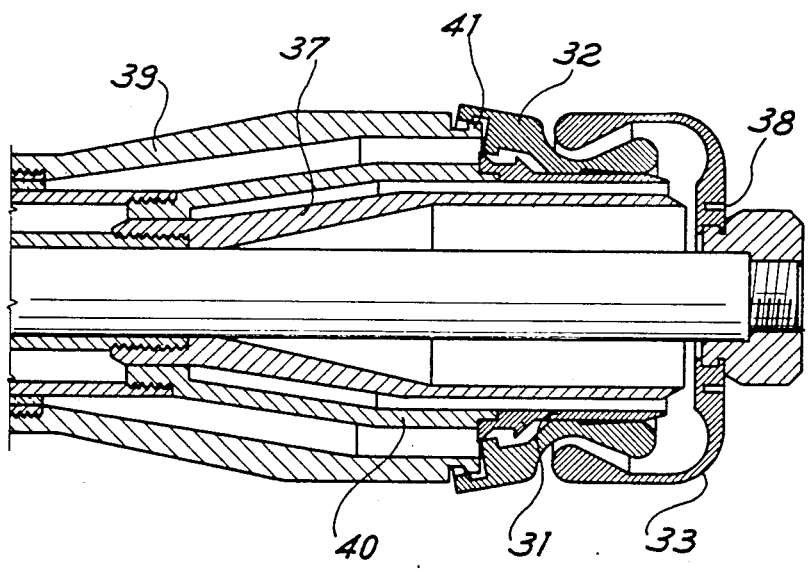
FIG. 2 is an enlarged side view of a modified head portion of FIG. 1.

The head portion of the mechanical circular anastomotic gun of FIG. 1 may be modified as shown in details in enlarged scale, in FIG. 2. The elements 39 and 40 carrying respectively the elements 32 and 31 of the compression suturing device for effecting the anastomosis, show a different outline than the corresponding elements in FIG. 1, particularly the element 39 at the end opposite to the threaded portion which has an annular recess delimited outwardly by a circular ledge 41 for the engagement with a corresponding matching ledge of an element of a suitable suturing device.

The mechanical anastomotic gun having the head portion as illustrated in FIG. 2, after the suturing device assembly has been moved forward and the tissue edges cut by means of blade 37 in connection with the groove 38 on the element 33, is separated from the assembled suturing device more easily then the gun of FIG. 1 and is easily pulled out of the hollow organ.

In use, the circular mechanical anastomotic gun according to the invention (reference is made in particular to the embodiment of FIG. 1, but obviously operation is extended to the device modified as indicated in FIG. 2) is inserted through a suitable aperture into the hollow organ dissected and by a rotation of the knob 20, the elements 2 and 3 are suitably spaced from each other. The purse-string suture placed on the tissue edge of the dissected organ immediately above the member 2, is tightened, then the element 3 is inserted inside the edge of the close hollow dissected organ the margins of which are stiched with another purse-string suture, and this suture is tightened on the central pivot 4, immediately below the element 3. With reversed operation of the knob 20, the elements 2 and 3 are positioned one inserted into the other, then the arms of the mechanical anastomotic gun are operated to shift the element 1 and the circular blade 7.

The element 1 and the circular blade 7 move together simultaneously until the element 1 reaches its final position fixing itself inside the element 2; then the circular blade 7 continues its movement and after having edged the purse-string sutures, it cuts the element 3 in connection with the groove 8.

The circular mechanical anastomotic gun is then drawn out and the suturing device remains positioned inside the hollow organ, from which it will separate only when the necrosis of the tissues occurs which follows the information of a natural suture between the tissue edges mating immediately out the area where the compression was applied.

What we claim is:

1. A circular mechanical anastomotic gun for insertion of a three-element device to effect compression anastomosis of hollow organs, comprising:

a main body having a groove and a recess intersecting said groove;

an outer tubular body having one end fixed to said main body and having another end for carrying an intermediate element of said device, said main body groove extending coaxially with said outer tubular body;

a movable driving means movably mounted in said main body;

means for moving said driving means axially of said outer tubular body;

an inner tubular body located coaxially within said outer tubular body and being affixed at one end thereof to said movable driving means to be moved thereby;

knife means affixed to another end of said inner tubular body and located adjacent to said intermediate element of said device;

an intermediate tubular body located coaxially with and between said inner and outer tubular bodies, said intermediate tubular body having one end for carrying an inner element of said device adjacent to said intermediate element of said device, and stop means mounted near another end of said intermediate tubular body; said stop means slidably engaging said main body along said groove and placing said intermediate tubular body into contact with said driving means to be moved by said driving means in conjunction with said inner tubular body;

disconnecting means for disconnecting said intermediate tubular body from said driving means, said disconnecting means including said main body recess which is sized to accomodate said stop means and located to receive said stop means after said driving means has moved a prescribed distance, said main body groove and recess being sized so that when said stop means are located in said main body recess, said intermediate tubular body is disconnected from said driving means; whereby said inner tubular body and said intermediate tubular body move conjointly for said predetermined distance and then said inner tubular body moves axially relative to said intermediate tubular body;

a central slide extending coaxially within said inner tubular body and having an adjusting means on one end for moving said central slide axially of said main body, said central slide having another end for carrying an outer element of said device to be moved into abutting contact with said intermediate element by movement of said central slide; and blocking means connecting said outer element of said device to said central slide, said blocking means being located and sized to be released from said outer element by said knife means when said inner tubular body has moved a predetermined distance after said intermediate tubular body has been disengaged from said driving means.

2. The circular mechanical anastomotic gun defined in claim 1 wherein said outer tubular body includes an annular recess having a circular ledge for engaging a corresponding annular recess and circular ledge of said intermediate element.

3. The circular mechanical anastomotic gun defined in claim 1 wherein said stop means includes a ramp and said main body portion includes a ramp engaging surface adjacent to said recess for guiding said stop means into and out of said main body recess.

4. A circular mechanical anastomotic gun suitable for the insertion of a three-element device to effect compression anastomosis of hollow organs, comprising:

a central slide carrying at an end thereof blocking means for carrying an outer element of said device; three tubular bodies coaxial with the central slide, which carry at their ends a circular blade, an inner and an intermediate element of said device, respectively; means for moving driving means coaxial with the central slide, said driving means being in engagement simultaneously with the inner tubular body carrying the circular blade and the intermediate tubular body carrying the inner element of said device; means disconnecting the engagement between said driving means and the intermediate tubular body after the intermediate tubular body has moved a prescribed distance with the inner element against the intermediate element, said driving means continuing to move only the inner tubular body so that the circular blade advances, cutting the outer element circumferentially outside said blocking means.

* * * * *